(12) United States Patent
Pigg et al.

(10) Patent No.: US 11,141,318 B2
(45) Date of Patent: *Oct. 12, 2021

(54) WOUND DRESSING WITH ADHESIVE MARGIN

(71) Applicant: KCI USA, Inc., San Antonio, TX (US)

(72) Inventors: William Pigg, Elvington (GB); Michelle Delbono, Earby (GB); Sally Stephens, Skipton (GB)

(73) Assignee: KCI USA, INC., San Antonio, TX (US)

( * ) Notice: Subject to any disclaimer, the term of this patent is extended or adjusted under 35 U.S.C. 154(b) by 875 days.

This patent is subject to a terminal disclaimer.

(21) Appl. No.: 15/659,486

(22) Filed: Jul. 25, 2017

(65) Prior Publication Data

US 2018/0021180 A1   Jan. 25, 2018

Related U.S. Application Data

(63) Continuation of application No. 14/653,760, filed as application No. PCT/IB2013/060862 on Dec. 12, 2013, now Pat. No. 10,271,995.

(30) Foreign Application Priority Data

Dec. 18, 2012   (GB) ..................................... 1222770

(51) Int. Cl.
*A61F 13/02* (2006.01)
*A61F 13/15* (2006.01)

(52) U.S. Cl.
CPC ...... *A61F 13/0263* (2013.01); *A61F 13/0203* (2013.01); *A61F 13/0206* (2013.01);
(Continued)

(58) Field of Classification Search
CPC .............. A61F 13/0203; A61F 13/0206; A61F 13/0246; A61F 13/025; A61F 13/0253;
(Continued)

(56) References Cited

U.S. PATENT DOCUMENTS

| 1,355,846 A | 10/1920 | Rannells |
| 1,944,834 A * | 1/1934 | Bennett, Jr. ........... A61F 13/023 428/139 |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery.

(Continued)

*Primary Examiner* — Bradley H Philips
(74) *Attorney, Agent, or Firm* — Foley & Lardner LLP

(57) ABSTRACT

A wound dressing comprising: a backing sheet; a layer of pressure-sensitive adhesive on the backing sheet; an island of absorbent material having smaller area than the backing sheet and applied onto a central region of the backing sheet so as to leave a margin of adhesive-coated backing sheet around the absorbent material, and an apertured wound facing layer applied over the absorbent material and adhered to the backing sheet around said island by said pressure-sensitive adhesive, wherein the apertured wound facing layer comprises an apertured substrate having a coating of a silicone gel on the wound facing surface thereof, the open area of the apertured wound facing layer is from about 5% to about 75%, and the apertured wound facing layer comprises apertures having an open area of from about 2 mm2 to about 100 mm².

27 Claims, 5 Drawing Sheets

(52) U.S. Cl.
CPC ...... *A61F 13/0246* (2013.01); *A61F 13/0253* (2013.01); *A61F 13/0289* (2013.01); *A61F 13/15707* (2013.01); *A61F 13/025* (2013.01); *A61F 2013/15715* (2013.01)

(58) Field of Classification Search
CPC .............. A61F 13/0263; A61F 13/0289; A61F 13/15707; A61F 2013/15715; A61F 13/0259–0266
See application file for complete search history.

(56) References Cited

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,967,624 A | 7/1976 | Milnamow |
| 3,983,297 A | 9/1976 | Ono et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,001 A * | 7/1986 | Gilman ................ A61F 13/023 602/52 |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,501,212 A | 3/1996 | Psaros |
| 5,512,041 A | 4/1996 | Bogart |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,634,893 A | 6/1997 | Rishton |
| 5,636,643 A | 6/1997 | Argenta et al. |
| 5,641,506 A | 6/1997 | Talke et al. |

(56) References Cited

U.S. PATENT DOCUMENTS

| | | |
|---|---|---|
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,776,119 A | 7/1998 | Bilbo et al. |
| 5,807,295 A | 9/1998 | Hutcheon et al. |
| 5,919,476 A | 7/1999 | Fischer et al. |
| 5,941,863 A | 8/1999 | Guidotti et al. |
| 5,981,822 A | 11/1999 | Addison |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 8,298,197 B2 | 10/2012 | Eriksson et al. |
| 8,529,532 B2 | 9/2013 | Pinto et al. |
| 8,632,523 B2 | 1/2014 | Eriksson et al. |
| 8,764,732 B2 | 7/2014 | Hartwell |
| 9,192,444 B2 | 11/2015 | Locke et al. |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0090085 A1 | 4/2008 | Kawate et al. |
| 2008/0119802 A1 | 5/2008 | Riesinger |
| 2008/0149104 A1 | 6/2008 | Eifler |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216204 A1 | 8/2009 | Bhavaraju et al. |
| 2009/0227969 A1 | 9/2009 | Jaeb et al. |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326488 A1 | 12/2009 | Budig et al. |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0185163 A1 | 7/2010 | Heagle |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0305490 A1 | 12/2010 | Coulthard et al. |
| 2010/0305524 A1 | 12/2010 | Vess et al. |
| 2010/0324516 A1 | 12/2010 | Braga et al. |
| 2011/0046585 A1 | 2/2011 | Weston |
| 2011/0112458 A1 | 5/2011 | Holm et al. |
| 2011/0137271 A1 | 6/2011 | Andresen et al. |
| 2011/0160686 A1* | 6/2011 | Ueda ............ A61F 13/0203 604/365 |
| 2011/0171480 A1 | 7/2011 | Mori et al. |

(56) References Cited

U.S. PATENT DOCUMENTS

| | | |
|---|---|---|
| 2011/0172617 A1 | 7/2011 | Riesinger |
| 2011/0224631 A1 | 9/2011 | Simmons et al. |
| 2011/0224634 A1* | 9/2011 | Locke ............... A61F 13/00029 604/319 |
| 2011/0229688 A1 | 9/2011 | Cotton |
| 2011/0244010 A1 | 10/2011 | Doshi |
| 2011/0257617 A1 | 10/2011 | Franklin |
| 2012/0016322 A1 | 1/2012 | Coulthard et al. |
| 2012/0123359 A1 | 5/2012 | Reed |
| 2012/0143157 A1 | 6/2012 | Riesinger |
| 2012/0258271 A1 | 10/2012 | Maughan |
| 2013/0030394 A1 | 1/2013 | Locke et al. |
| 2013/0066285 A1 | 3/2013 | Locke et al. |
| 2013/0096518 A1 | 4/2013 | Hall et al. |
| 2013/0152945 A1 | 6/2013 | Locke et al. |
| 2014/0012213 A1* | 1/2014 | Locke ................. A61F 13/0216 604/319 |
| 2014/0039423 A1 | 2/2014 | Riesinger |
| 2014/0039424 A1 | 2/2014 | Locke |
| 2014/0058309 A1* | 2/2014 | Addison ........... A61F 13/00029 602/44 |
| 2014/0155849 A1 | 6/2014 | Heaton et al. |
| 2014/0171851 A1 | 6/2014 | Addison |
| 2014/0309574 A1 | 10/2014 | Cotton |
| 2014/0350494 A1 | 11/2014 | Hartwell et al. |
| 2015/0030848 A1 | 1/2015 | Goubard |
| 2015/0119830 A1 | 4/2015 | Luckemeyer et al. |
| 2015/0190286 A1 | 7/2015 | Allen et al. |
| 2016/0067107 A1 | 3/2016 | Cotton |

FOREIGN PATENT DOCUMENTS

| | | | |
|---|---|---|---|
| AU | 755496 B2 | 12/2002 | |
| AU | 2009200608 A1 | 10/2009 | |
| CA | 2005436 A1 | 6/1990 | |
| CN | 87101823 A | 8/1988 | |
| DE | 26 40 413 A1 | 3/1978 | |
| DE | 43 06 478 A1 | 9/1994 | |
| DE | 29 504 378 U1 | 9/1995 | |
| DE | 202004018245 U1 | 7/2005 | |
| EP | 0097517 A1 | 1/1984 | |
| EP | 0100148 A1 | 2/1984 | |
| EP | 0117632 A2 | 9/1984 | |
| EP | 0161865 A2 | 11/1985 | |
| EP | 0251810 A2 | 1/1988 | |
| EP | 0275353 A2 | 7/1988 | |
| EP | 0358302 A2 | 3/1990 | |
| EP | 0538917 A1 | 4/1993 | |
| EP | 0630629 A1 | 12/1994 | |
| EP | 0659390 A2 | 6/1995 | |
| EP | 0633758 B1 | 10/1996 | |
| EP | 1002846 A1 | 5/2000 | |
| EP | 1018967 A1 | 7/2000 | |
| EP | 2578193 A1 | 4/2013 | |
| GB | 692578 A | 6/1953 | |
| GB | 1386800 A | 3/1975 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| GB | 2377939 A | 1/2003 | |
| GB | 2392836 A | 3/2004 | |
| GB | 2393655 A | 4/2004 | |
| GB | 2425487 A | 11/2006 | |
| GB | 2452720 A | 3/2009 | |
| GB | 2496310 A | 5/2013 | |
| JP | 1961003393 | 2/1961 | |
| JP | S62139523 U | 9/1987 | |
| JP | S62-275456 A | 11/1987 | |
| JP | 08-336555 A | 12/1996 | |
| JP | 2007254515 A | 10/2007 | |
| JP | 2008080137 A | 4/2008 | |
| JP | 4129536 B2 | 8/2008 | |
| JP | 2015501712 A | 1/2015 | |
| SG | 71559 | 4/2002 | |
| WO | 80/02182 A1 | 10/1980 | |
| WO | 87/04626 A1 | 8/1987 | |
| WO | 8707164 A1 | 12/1987 | |
| WO | 90/010424 A1 | 9/1990 | |
| WO | 93/009727 A1 | 5/1993 | |
| WO | WO-93/13813 A1 | 7/1993 | |
| WO | WO-93/19709 A1 | 10/1993 | |
| WO | 94/020041 A1 | 9/1994 | |
| WO | WO-95/15135 A1 | 6/1995 | |
| WO | 96/05873 A1 | 2/1996 | |
| WO | 9622753 A1 | 8/1996 | |
| WO | 97/18007 A1 | 5/1997 | |
| WO | 99/13793 A1 | 3/1999 | |
| WO | 99/65542 A1 | 12/1999 | |
| WO | 01/36188 A1 | 5/2001 | |
| WO | 01/60296 A1 | 8/2001 | |
| WO | 0168021 A1 | 9/2001 | |
| WO | 0185248 A1 | 11/2001 | |
| WO | WO-02/20067 A2 | 3/2002 | |
| WO | 0243743 A1 | 6/2002 | |
| WO | 02062403 A1 | 8/2002 | |
| WO | 03-018098 A2 | 3/2003 | |
| WO | WO-03/043553 A1 | 5/2003 | |
| WO | 03045294 A1 | 6/2003 | |
| WO | 03045492 A1 | 6/2003 | |
| WO | 03053484 A1 | 7/2003 | |
| WO | 2004024197 A1 | 3/2004 | |
| WO | 2004037334 A1 | 5/2004 | |
| WO | WO-2004/060359 A1 | 7/2004 | |
| WO | WO-2004/060413 A1 | 7/2004 | |
| WO | 2004112852 A1 | 12/2004 | |
| WO | 2005002483 A2 | 1/2005 | |
| WO | 2005062896 A2 | 7/2005 | |
| WO | 2005105176 A1 | 11/2005 | |
| WO | 2005123170 A1 | 12/2005 | |
| WO | 2007022097 A2 | 2/2007 | |
| WO | 2007030601 A2 | 3/2007 | |
| WO | 2007070269 A1 | 6/2007 | |
| WO | 2007085396 A1 | 8/2007 | |
| WO | 2007087811 A1 | 8/2007 | |
| WO | 2007113597 A2 | 10/2007 | |
| WO | WO-2007113597 A2 * | 10/2007 | ......... A61F 13/0226 |
| WO | 2007133618 A2 | 11/2007 | |
| WO | 2008041926 A1 | 4/2008 | |
| WO | 2008054312 A1 | 5/2008 | |
| WO | WO-2008/062176 A1 | 5/2008 | |
| WO | 2008/082444 A2 | 7/2008 | |
| WO | 2008/100440 A1 | 8/2008 | |
| WO | 2008104609 A1 | 9/2008 | |
| WO | 2008/131895 A1 | 11/2008 | |
| WO | 2009/002260 A1 | 12/2008 | |
| WO | 2008149107 A1 | 12/2008 | |
| WO | 2009066105 A1 | 5/2009 | |
| WO | 2009066106 A1 | 5/2009 | |
| WO | WO-2009/067062 A1 | 5/2009 | |
| WO | 2009081134 A1 | 7/2009 | |
| WO | 2009089016 A1 | 7/2009 | |
| WO | 2009/124100 A1 | 10/2009 | |
| WO | 2009126103 A1 | 10/2009 | |
| WO | 2010032728 A1 | 3/2010 | |
| WO | 2010056977 A2 | 5/2010 | |
| WO | WO-2010/061228 A1 | 6/2010 | |
| WO | WO-2010/122665 A1 | 10/2010 | |
| WO | 2010129299 A2 | 11/2010 | |
| WO | 2011008497 A2 | 1/2011 | |
| WO | 2011/049562 A1 | 4/2011 | |
| WO | 2011043786 A1 | 4/2011 | |
| WO | 2011115908 A1 | 9/2011 | |
| WO | 2011121127 A1 | 10/2011 | |
| WO | 2011162862 A1 | 12/2011 | |
| WO | 2012/112204 A1 | 8/2012 | |
| WO | 2012104584 A1 | 8/2012 | |
| WO | 2012140378 A1 | 10/2012 | |
| WO | 2012143665 A1 | 10/2012 | |
| WO | WO-2012/140378 A1 | 10/2012 | |
| WO | 2013009239 A1 | 1/2013 | |

(56) References Cited

FOREIGN PATENT DOCUMENTS

| | | | |
|---|---|---|---|
| WO | 2013090810 A1 | 6/2013 | |
| WO | 2014039557 A1 | 3/2014 | |
| WO | 2014/113253 A1 | 7/2014 | |
| WO | 2014140608 A1 | 9/2014 | |
| WO | 2014143488 A1 | 9/2014 | |
| WO | 2015/065615 A1 | 5/2015 | |
| WO | 2015130471 A1 | 9/2015 | |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp: 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp: 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.

(56) References Cited

OTHER PUBLICATIONS

International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
International Search Report and Written opinion dated Dec. 15, 2009; PCT Internation Application No. PCT/US2009/036222.
Response filed Oct. 20, 2011 for U.S. Appl. No. 12/398,904.
Interview Summary dated Oct. 27, 2011 for U.S. Appl. No. 12/398,904.
Non-Final Office Action dated dated Jul. 20, 2011 for U.S. Appl. No. 12/398,904.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
NDP 1000 Negative Pressure Wound Terapy System, Kalypto Medical, pp. 1-4.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
NPD 1000 Negative Pressure Would Therapy System, Kalypto Medical, pp. 1-4.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Examination Report dated Jun. 29, 2016, corresponding to EP Application No. 16173614.5.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion date dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
International Search Report and Written Opinion for corresponding PCT application PCT/US2016/051768 dated Dec. 15, 2016.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.

* cited by examiner

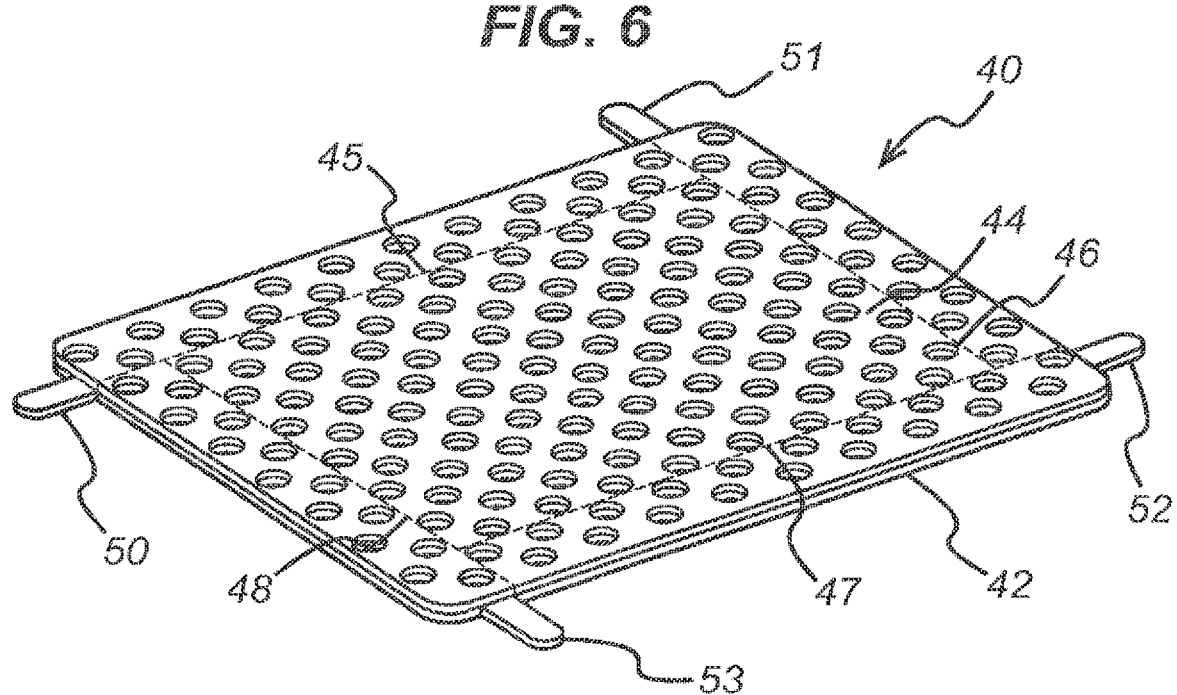
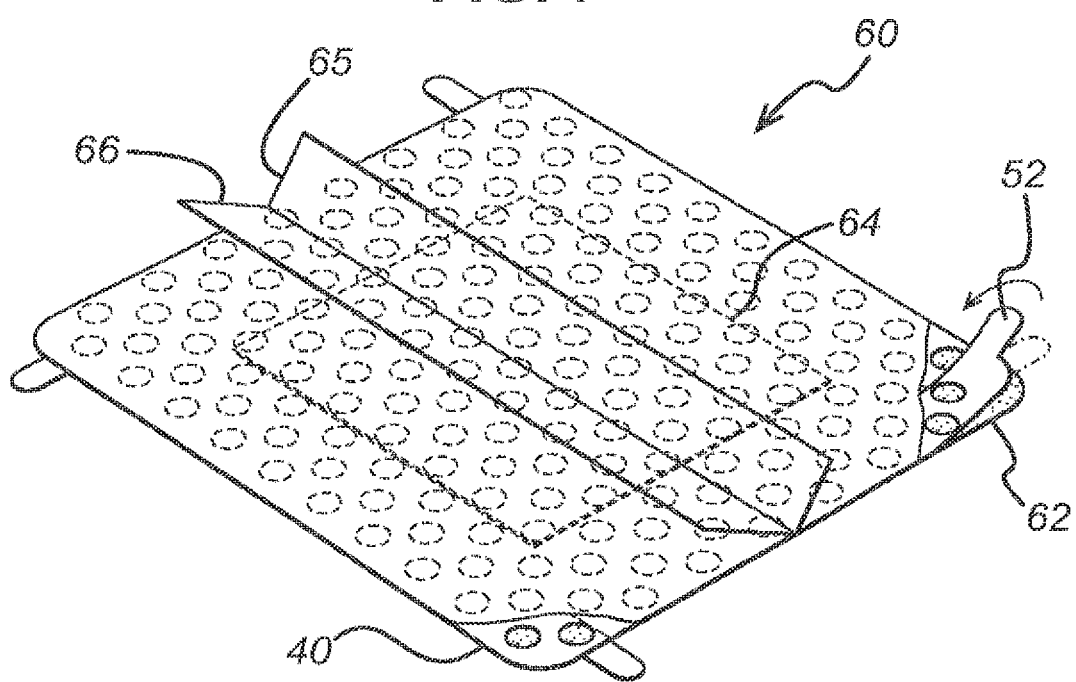

WOUND DRESSING WITH ADHESIVE MARGIN

This application is a continuation of U.S. Non-Provisional patent application Ser. No. 14/653,760 filed on Jun. 18, 2015, entitled "Wound Dressing with Adhesive Margin," which claims the priority benefit of PCT Application No. PCT/I132013/060862, filed on Dec. 12, 2013, which claims the priority benefit of GB 1222770.8, filed on Dec. 18, 2012, all of which are incorporated herein by reference for all purposes.

The present invention relates to island-type wound dressings.

Island-type wound dressings comprise an absorbent region and an adhesive backing sheet covering the absorbent region and extending beyond the edges of the absorbent region to provide an adhesive margin around the absorbent region for attachment of the dressing to intact skin around the wound to be treated. The adhesive margin provides secure attachment of the dressing without the need for secondary dressings such as a bandage. The adhesive margin also reduces or prevents leakage of wound exudate from the edges of the dressing.

The adhesive used in such dressings is typically a medically acceptable pressure-sensitive adhesive (PSA) such as an acrylic-based PSA. Such adhesives provide a strong bond to skin, but as a result they are not readily repositionable, and they may cause skin irritation and/or discomfort when the dressing is removed. Moreover, the PSA is not normally permeable to oxygen or water vapour and therefore interferes with normal skin transpiration.

It is known to provide a discontinuous, e.g. patterned, layer of the PSA in order to address the above problems. However, application of a patterned layer of PSA increases the complexity of the manufacturing process and increases the risk of liquid leakage through the PSA to the edges of the dressing.

In a first aspect, the present invention provides a wound dressing comprising: a backing sheet, a layer of pressure-sensitive adhesive on the backing sheet; an island of absorbent material having smaller area than the backing sheet and applied onto a central region of the backing sheet so as to leave a margin of adhesive-coated backing sheet around the absorbent material, and an apertured wound lacing layer applied over the absorbent material and adhered to the backing sheet around said island by said pressure-sensitive adhesive, wherein the apertured wound facing layer comprises an apertured substrate having a coating of a silicone elastomer on the wound facing surface thereof, the open area of the apertured wound facing layer is from about 5% to about 75%, and the aperture wound facing layer-comprises apertures having an open area of from about 2 mm$^2$ to about 100 mm$^2$.

The adhesive-coated backing sheet may have any shape, such as square, rectangular, circular, oval, trapezium-shaped, suitably with rounded corners.

The adhesive-trolled hacking sheet supports the absorbent island and suitably provides a barrier to passage of microorganisms through the dressing. Suitably, the adhesive-coated backing sheet is substantially liquid-impermeable. The adhesive-coated backing sheet is suitably semipermeable. That is to say, the adhesive-coated backing sheet is suitably permeable to water vapour, but not permeable to liquid water or wound exudate. Suitably, the adhesive-coated backing sheet is also microorganism-impermeable. Suitable continuous conformable adhesive-coated backing sheets will suitably have a moisture vapor transmission rate (MVTR) of the backing sheet alone of 300 to 30000 g/m$^2$/24 hrs, suitably 1000 to 1500 g/m$^2$/24 hrs, and in one embodiment 1000 to 5000 g/m$^2$/24 hrs, at 37.5° C. at 100% to 10% relative humidity difference. The adhesive-coated backing sheet thickness is suitably in the range of 10 to 1000 micrometers, more suitably 100 to 500 micrometers.

Suitable polymers for forming the adhesive-coated backing sheet include polyurethanes and poly alkoxyalkyl acrylates and methacrylates such as those disclosed in GB-A-1280631. Suitably, the adhesive-coated backing sheet comprises a continuous layer of a high density blocked polyurethane foam that is predominantly closed-cell. A suitable adhesive-coated backing sheet material is the polyurethane film available under the Registered Trade Mark ESTANE 5714F. Also suitable are elastomeric polymeric esters such as Du Pont HYTREL (Registered Trade Mark).

The absorbent island may comprise any of the layers conventionally used for absorbing wound fluids, serum or blood in the wound healing art, including gauzes, nonwoven fabrics, superabsorbents, hydrogels and mixtures thereof. Suitably, the absorbent island comprises a layer of hydrophilic polyurethane foam on a wound facing side thereof, such as an open celled hydrophilic polyurethane foam prepared in accordance with EP-A-0541391. The absorbent island may further comprise a wicking layer. This may be a layer of a nonwoven fibrous web, for example a carded web of viscose staple fibers. The basis weight of the absorbent layer may suitably be in the range of 50-500 g/m$^2$, such as 100-400 g/m$^2$. The uncompressed thickness of the absorbent layer may be in the range of from 0.5 mm to 10 mm, such as 1 mm to 4 mm. The free (uncompressed) liquid absorbency measured for physiological saline may suitably be in the range of 5 to 30 g/g at 25° C.

The area of the absorbent island is suitably in the range of from 1 cm$^2$ to 400 cm$^2$, more suitably from 4 cm$^2$ to 200 cm$^2$, still more suitably from about 10 cm$^2$ to about 150 cm$^2$, for example from about 16 cm$^2$ to about 100 cm$^2$. Dressings of the latter size are especially suitable for the treatment of leg ulcers.

The island has a smaller area than the adhesive-coated backing sheet such that an adhesive-coated margin of the backing sheet extends around the island. Normally, the adhesive-coated margin extends around every edge of the absorbent island. Suitably, the adhesive-coated margin has a mean width of from 0.5 to 5 cm, suitably from 1 to 3 cm. The adhesive-coated margin may be made up of an inner margin covered by the apertured coated layer, and an outer margin extending outside the apertured coated layer, as explained further below.

The pressure-sensitive adhesive layer is suitably pressure-sensitive adhesive layer of the type conventionally used for island-type wound dressings. The PSA layer is suitably a continuous layer, but it may be apertured or interrupted in some embodiments. Acrylic-based pressure sensitive adhesive are suitable. In embodiments, a pressure sensitive adhesive based on acrylate ester copolymers, polyvinyl ethyl ether and polyurethane as described for example in GB-A-1280631. The basis weight of the PSA layer is suitably 20 to 250 g/m$^2$, and more suitably 50 to 150 g/m$^2$.

The apertured layer having a coating of silicone elastomer provides a weakly adherent (tacky) or non-adherent wound facing layer over the absorbent layer. In addition, the apertured layer having a coating of silicone elastomer extends over at least part of the adhesive-coated margin. In this part of the margin, the apertured layer covers a portion of the PSA-coated surface of the backing sheet but allows adhesion of the pressure-sensitive adhesive through the apertures of the layer resulting in reduced overall adherency of the backlog sheet in this part of the margin. The overlap of the apertured coated layer and the adhesive-coated backing sheet around the absorbent layer also serves to attach the apertured coated layer to the backing sheet thereby securing the laminate. The silicone elastomer coating is suitably hydrophobic, whereby leakage of wound fluid through the edges of the dressing is inhibited. The silicone elastomer coating may be tacky or non-tacky.

The apertures in the apertured layer are suitably large enough to allow skin contact of the backing layer PSA through the apertures when the dressing is applied to skin around a wound. Suitably, the said apertures have an open area of from about 4 $mm^2$ to about 50 $mm^2$, for example from about 5 $mm^2$ to about 30 $mm^2$. This refers to the average (mean) area of the apertures. Suitably, at least about 90% of the apertures in the apertured layer have open area in the specified ranges. Suitably, at least about 90%, for example substantially all, of the apertures have substantially the same size and shape. Suitably, said apertures consist essentially of a regular array of apertures. The apertures may be of any shape, but suitably they are circular, oval or polygonal. Suitably, the open area of the apertured layer is from about 10% to about 70% of the total area, for example from about 20% to about 50% of the total area, for example about 25% to about 40% of the total area. Suitably, the density of the apertures is from about 1000 to about 100,000 apertures per $m^2$, for example about 5000 to about 50,000 apertures per $m^2$.

Likewise, in order to ensure sufficient adherency of the PSA through the apertures of the apertured layer, the apertured layer is suitably thin. In embodiments, the thickness of the apertured wound facing layer is less than about 1 mm, for example from about 0.02 mm to about 0.5 mm, in embodiments from about 0.05 mm to about 0.2 mm. The term "thickness" in this context refers to the combined thickness of the silicone coating and substrate.

The apertured substrate may be any medically acceptable apertured sheet material, including textile materials such as gauzes. Suitably, the apertured substrate is a unitary substrate such as a unitary polymer mesh or an apertured polymer film. Suitable polymer materials include polyethylene, polypropylene, polyester, polyvinyl acetate, and ethylene vinyl acetate. Suitably, the film substrate has a thickness of from about 1 μm to about 100 μm, for example from about 5 μm to about 25 μm. In other embodiment the substrate is a woven or nonwoven textile material, typically having an uncompressed thickness of from about 0.1 mm to about 1 mm.

In embodiments, the apertured wound facing layer is smaller than the adhesive-coated backing sheet, whereby an adhesive-coated margin of the backing sheet extends around the apertured wound facing layer. This continuous PSA margin provides additional security of attachment and leak resistance around the edges of the dressing. However, it can be made narrower than the PSA-coated margin of conventional island dressings because of the adherency of the inner margin covered by the apertured layer. Thus, in embodiments, the margin of PSA-coated backing sheet around the absorbent island that is covered by the apertured layer has a mean width of from about 5 mm to about 30 mm, for example from about 10 mm to about 20 mm. The outer margin of PSA-coated backing sheet only (where present) has a mean width of from about 2 mm to about 20 mm, for example from about 5 mm to about 15 mm, typically about 10 mm.

In embodiments, the apertured wound facing material comprises lines or weakness substantially parallel to, and spaced from, one or more edges of the apertured wound facing material. These lines of weakness define tear-off strips along one or more edges of the apertured wound facing material that allow the size of the apertured wound facing material (and hence the width of the PSA-coated margin around the outside of the apertured wound facing material) to be varied according to the clinical requirements. Thus, for a heavily-exuding wound, a wider PSA-coated margin around the edges of the dressing may be desirable. On the other hand, for lightly exuding wounds, or where easy repositioning of the dressing is desirable, little or no PSA-coated margin around the outside of the apertured wound facing material may be preferable. Thus, in some embodiments the apertured wound facing sheet may be coterminous with the PSA-coated backing sheet prior to removal of any of the tear strips so that there is no continuously PSA-coated margin around the apertured wound facing sheet until removal of the tear strips.

The lines of weakness may, for example comprise lines of perforations or score lines. Suitably, one or more lines of weakness defining tear-off strips are defined in all edges of the apertured wound facing material so as to allow uniform increasing of the PSA-coated margin. Suitably, the width of the tear-off strips (i.e. the average spacing of the lines of weakness from the edges of the apertured sheet is from about 5 mm to about 20 mm, for example about 8 mm to about 15 mm. Suitably, a pull tab is attached to, or formed integrally with, each tear strip defined by the lines of weakness to assist removal of the tear strip. Suitably, a release coating such as a silicone or a fluoropolymer coating may be provided on the underside of the tear-off strips of the apertured wound contacting layer to assist removal of the strips.

The silicone coating on the wound facing side of the apertured layer is suitably a hydrophobic, tacky or non-tacky silicone polymer. The silicone elastomer coating is suitably coated only on the wound facing side of the apertured layer.

The total coating weight of the silicone is suitably from about 15 $g/m^2$ to about 500 $g/m^2$, for example from about 40 $g/m^2$ to about 250 $g/m^2$, typically from about 50 $g/m^2$ to about 150 $g/m^2$. The silicone is suitably a soft skin adhesive silicone composition. Suitable chemistry is described below. The silicone is suitably hydrophobic.

Suitably, the silicone composition is a so-called soft skin adhesive silicone elastomer. Such silicones can be made by an addition reaction (hydrosilylation) between (a) a vinyl functional polydimethyl siloxane, such as bis-dimethyl vinyl polydimethylsiloxane (PDMS), and (b) a hydrogen functional siloxane, such as dimethyl, methylhydrogen siloxane copolymers, hydrogen dimethylsiloxy terminated PDMS. The cure reaction is catalyzed by a hydrosilylation catalyst, such as a noble metal catalyst, suitably a platinum catalyst. A silicone prepolymer composition may further comprise a polymerization inhibitor that is evaporated from said composition during said step of thermally partially curing, for example 2-methyl-3-butyn-2-ol. Where present, the polymerization inhibitor is suitably present in an amount of from about 0.001 wt. % to about 1 wt %, for example from about 0.01 wt % to about 0.1 wt. % before curing. Alternatively, no polymerisation inhibitor is present in the silicone compositions.

Silicone skin adhesive compositions are suitably supplied as two-part systems: Part A contains at least the vinyl prepolymer and the catalyst, while Part B contains the vinyl prepolymer and the SiH siloxane cross linker. The components are mixed immediately before use, optionally with addition of a polymerization inhibitor.

In embodiments, the silicone coating composition comprises or consists essentially of the following components:
(A) a diorganopolysiloxane having at least 2 alkenyl groups in each molecule;
(B) an organohydrogenpolysiloxane having at least 2 silicon-bonded hydrogen atoms in each molecule, in a quantity sufficient for the ratio between the number of moles of silicon-bonded hydrogen atoms in this component and the number of moles of alkenyl groups in component (A) to have a value of from about 0.6:1 to about 20:1.
(C) optionally a platinum group metal catalyst suitably in a quantity providing 0.1 to 500 weight parts as platinum group metal per 1,000,000 weight parts component (A); and
(D) optionally, a volatile polymerization inhibitor, suitably selected from: alkyne alcohols such as 2-methyl-3-butyn-2-ol, 3,5-dimethyl-1-hexyn-3-ol, and phenylbutynol; ene-yne compounds such as 3-methyl-3-penten-1-yne and 3,5-dimethyl-3-hexen-1-yne; tetramethyhyltrahexenyl-cyclotetrasiloxane; and benzotriazole.

The diorganopolysiloxane, component (A), used in the instant invention is the base component of the total composition. This diorganopolysiloxane must contain at least 2 alkenyl groups in each molecule in order for this composition to cure into a rubbery elastic silicone rubber coating composition.

The diorganopolysiloxane (A) comprises essentially straight-chain organopolysiloxane with the average unit formula $R_nSiO_{(4-n)/2}$, wherein R is selected from substituted and unsubstituted monovalent hydrocarbon groups and n has a value of 1.9 to 2.1 R may be exemplified by alkyl groups such as methyl, ethyl, propyl, and others; alkenyl groups such as vinyl, allyl, and others; aryl groups such as phyenyl, and others; and haloalkyl groups such as 3,3,3-trifluoropropyl and others. The diorganopolysiloxane (A) should have a viscosity at 25° C. of at least 100 centipoise (1 d Pa·s). When such factors as the strength of the silicone rubber coating membrane, and blendability are taken into account, the viscosity of diorganopolysiloxane (A) at 25° C. is preferably from 1,000 centipoise (1 Pa·s) to 100,000 centipoise (100 Pa·s). The diorganopolysiloxane (A) may be exemplified by dimethylvinylsiloxy-endblocked dimethylpolysiloxanes, dimethylvinylsiloxy-endblocked dimethylsiloxane-methylvinylsiloxane copolymers, and dimethylvinyl-siloxy-endblocked dimethylsiloxane-methylphenylsiloxane copolymers.

Component (B), an organopolysiloxane that contains at least 2 silicon-bonded hydrogen atoms in each molecule, is a crosslinker for the composition of the instant invention. The organopolysiloxane (B) may be exemplified by trimethylsiloxy-endblocked methylhydrogenpolysiloxanes, trimethylsiloxy-endblocked dimethylsiloxanemethylhydrogensiloxane copolymers, dimethylphenylsiloxy-endblocked methylphenylisloxanemethylhydrogensiloxane copolymers, cyclic methylhydrogenpolysiloxanes, and copolymers that contain the dimethylhydrogensiloxy unit and SiO4/2 unit. The organohydrogenpolysiloxane (B) should be added in a quantity that the ratio between the number of moles of silicon-bonded hydrogen atoms in this organohydrogenpolysiloxane and the number of moles of alkenyl groups in component (A) has a value of 0.6:1 to 20:1.

The platinum group metal catalyst, component (C), used in the compositions is a curing catalyst. The platinum group metal catalyst (C) may be exemplified by platinum micropowder, platinum black, chloroplatinic acid, platinum tetrachloride, olefin complexes of chloroplatinic acid, alcohol solutions of chloroplatinic acid, complexes between chloroplatinic acid and alkenylsiloxanes, rhodium compounds, and palladium compounds. The platinum group metal catalyst (C) should be added generally at 0.1 to 500 weight parts as platinum group metal per 1,000,000 weight parts component (A), and is preferably used at 1 to 50 weight parts as platinum group metal per 1,000,000 weight parts component (A). The reaction will not develop adequately at less than 0.1 weight parts, while additions in excess of 500 weight parts are uneconomical.

The coated substrate is then subjected to thermal curing to at least partially cure the silicone. The thermal curing is suitably performed continuously by passing the coated substrate through an oven. Suitable thermal curing conditions include exposure to a temperature of from about 80° C. to about 200° C., for example about 120° C. to about 180° C. for a time of from about 1 minute to about 10 minutes, for example about 1.5 minutes to about 5 minutes. The elevated temperature results in evaporation of any polymerization inhibitor from the silicone composition and therefore promotes polymerization of the silicone. The resulting material is chemically polymerized, but may be capable of further curing by ionizing radiation for example during sterilization.

The adhesive dressing according to the present invention may further comprise at least one removable cover sheet to cover the absorbent island and the adhesive-coated margin(s) around the absorbent island. The cover sheet covers and protects the absorbent island and prevents premature adhesion of the adhesive layer. The cover sheet is removed by the care giver immediately before application of the dressing.

The cover sheet may comprise a film of polyethylene, polypropylene or fluorocarbons and papers coated with these materials. Suitably, the cover sheet is a release-coated paper sheet, such as a silicone, release-coated paper sheet. Examples of silicone-coated release papers are POLYSLIK (Registered Trade Mark) supplied by H.P. Smith & Co., offered in various formulations to control the degree of adhesion of the paper to the adhesive surface.

Suitably, the dressing comprises a first removable cover sheet having a first edge and a second removable cover sheet that meets the first cover sheet along the first edge.

Certain suitable dressings have a central cover sheet with first and second opposed edges, and two side cover sheets that meet the central cover sheet along the opposed edges. Suitably, the opposed edges are substantially parallel. This arrangement of three cover sheets is especially suitable for positioning of relatively large dressings, such as sacral dressings, as described in detail in EP-A-0117632.

Suitably, along each of said edges where the cover sheets meet, one of the cover sheets is folded back to provide a folded-back margin, and the other cover sheet overlaps the said folded-back margin. This provides art easy-to-grasp margin on each cover sheet in the region of overlap to assist removal of the cover sheets by the care giver.

In the case of the embodiment comprising three cover sheets described above, each side cover sheet is suitably folded back along each of said edges where the cover sheets meet to provide a folded-back margin, and the central cover sheet overlaps the said folded-back margin, suitably as described in EP-A-0117632.

Suitably the dressing according to the present invention is sterile and packaged in a microorganism-impermeable container.

The dressing of the invention may be made by conventional cutting and lamination of the various layers. The apertured coated top sheet may be made by coating a suitable film substrate with a fluid silicone precursor mixture as described above, followed by thermal curing as described above. The coating may be done by any conventional means, such as by roller, doctor blade, spraying or dipping. In embodiments, the fluid silicone precursor may be coated onto an already-apertured substrate, in which case the coated substrate is suitably passed over an air blower to blow excess precursor out of the apertures as described for example in WO-A-9319709.

In other embodiments, the film substrate may be apertured, for example by die cutting, for example after the coating and curing steps. In a particularly suitably embodiment, the die cutting is performed after curing of a layer of the silicone sandwiched between the support film and a release sheet.

Accordingly, in a further aspect the present invention provides a method of making a wound dressing as described herein comprising the steps of forming a precursor laminate comprising a layer of silicone sandwiched between a polymeric film support sheet and a release sheet; die cutting aperture perimeters through the polymeric film support sheet and the silicone layer; and removing the release sheet to leave an apertured wound facing layer comprising an apertured polymeric film having a coating of a silicone gel on the wound facing surface thereof.

In a further aspect the present invention provides a method of making a wound dressing as described herein comprising the steps of: forming a precursor laminate comprising a layer of a fluid silicone prepolymer sandwiched between a polymeric film support sheet and a release sheet; curing said fluid silicone prepolymer; die cutting aperture perimeters through the polymeric film support sheet and the silicone layer; and removing the release sheet to leave an apertured wound facing layer comprising an apertured polymeric film having a coating of a silicone gel on the wound facing surface thereof.

In a further aspect the present invention provides a method of making a wound dressing as described herein comprising the steps of: forming a precursor laminate comprising a layer of silicone sandwiched between a polymeric film support sheet and a release sheet, wherein said precursor laminate is formed by disposing a layer of a fluid silicone prepolymer on said release sheet, curing said fluid silicone prepolymer, and disposing said polymeric film support sheet on the silicone layer; die cutting aperture perimeters through the polymeric film support sheet and rite silicone layer; and removing the release sheet to leave an aperatured wound facing layer comprising an apertured polymeric film having a coating of a silicone gel on the wound facing surface thereof.

Suitably, the method according to the present invention further comprises one or more of the following steps: coating one surface of a backing sheet with a layer of pressure sensitive adhesive; applying an island of absorbent material to a central region of the adhesive-coated surface of the backing sheet, wherein the absorbent material has a smaller area than the backing sheet so as to leave an adhesive-coated margin of the backing sheet around the island; and applying said apertured wound facing layer over said island with said polymeric film support sheet facing the backing sheet, wherein a margin of said wound contacting laminate is adhered to said adhesive-coated margin around said island.

Suitably, the method further comprises the step of packaging the dressing in a microorganism-impermeable container, and sterilizing the dressing. Sterilization may be, and preferably is, effected using an ethylene oxide (EtO) sterilization process, which is known in the art for sterilization of medical and pharmaceutical products that cannot support conventional high temperature steam sterilization in a typical process, gaseous EtO is mixed with air at a ratio of at least 3% EtO and infiltrates the dressing to kill any microorganisms remaining from the production process. Most EtO sterilization processes involve a pre-conditioning stage, a sterilization stage and a degassing stage.

Sterilization may also be effected with ionizing radiation, such as gamma radiation Commercially available gamma irradiation equipment includes equipment often used for gamma irradiation sterilization of products for medical applications. Cobalt 60 sources are appropriate. Total absorbed doses are suitably from 20 to 60 kGy, more suitably from about 35 to 50 kGy and dose rates are suitably about 7 to 8 kGy/hour. It has been (bund that the ionizing radiation provides a further benefit of further curing the silicone elastomer.

The methods of the invention may be used to make any products according to the invention. Any feature disclosed herein in relation to any one or more aspects of the invention is suitable for use in any of the other aspects defined herein.

Embodiments of the present invention will now be described by way of example with reference to the accompanying drawings, in which:

FIG. 6 shows a perspective view of an apertured top sheet incorporating tear strips;

FIG. 7 shows a bottom perspective view of a dressing according to a second embodiment of the present invention, incorporating the apertured top sheet of FIG. 6.

Figure 1:
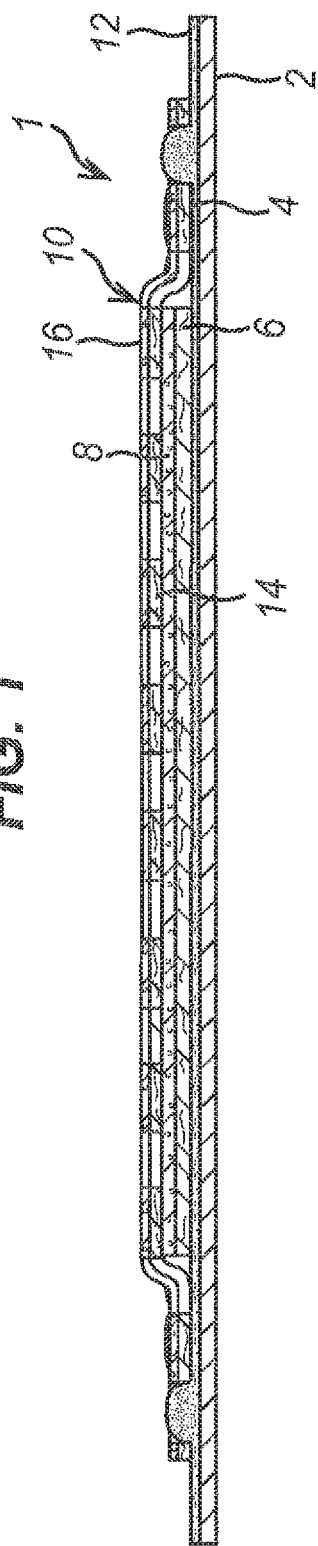
FIG. 1 shows a longitudinal cross-section through a dressing according to the invention.
Figure 2:
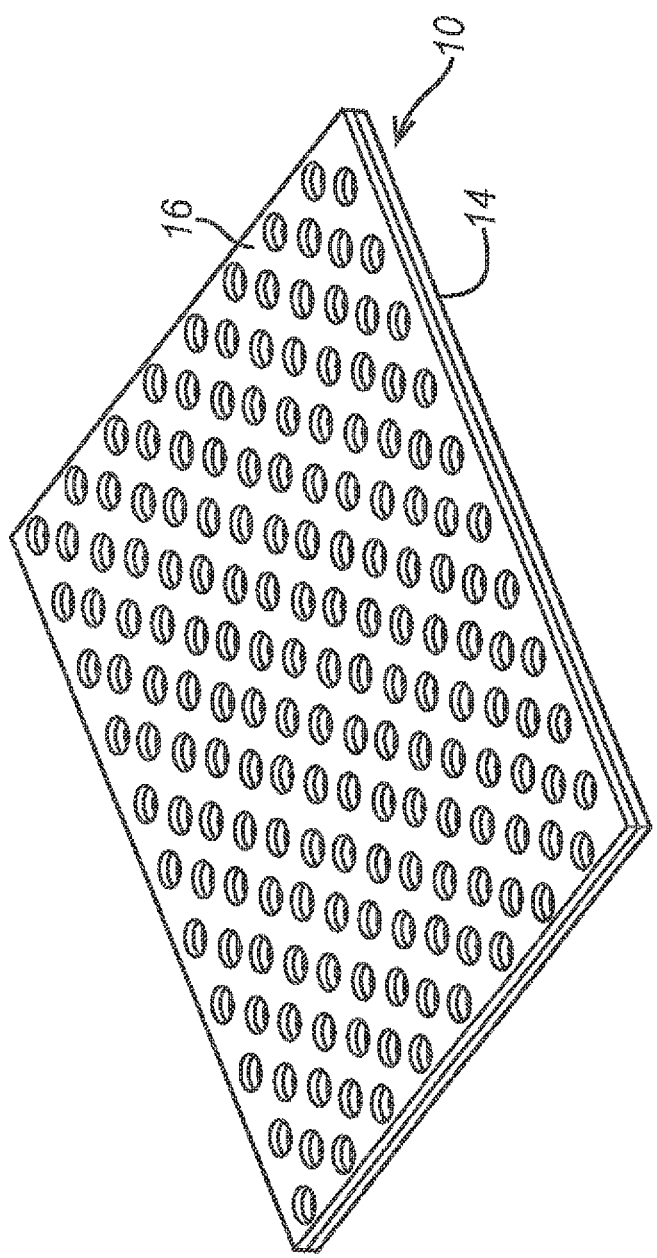
FIG. 2 shows a perspective view of the apertured top sheet of the dressing of FIG. 1.

Referring to FIGS. 1 to 4, the wound dressing 1 according to the invention comprises a conventional backing sheet 2 of microporous, semipermeable polyurethane. The backing sheet 2 is coated on its wound-facing surface with a continuous layer 4 of medically acceptable acrylic pressure-sensitive adhesive. An absorbent island is located in the central region of the wound-facing surface of the backing sheet 2 so as to leave an adhesive-coated margin of the backing sheet 2 around the island. The absorbent island is made up of nonwoven textile absorbent/wicking layer 6 and a polyurethane foam wound facing layer 8. Each of these layers is 1-2 mm thick in the dry uncompressed state, i.e. before use. The absorbent/wicking layer 6 is formed of viscose fibers optionally mixed with gel-forming fibers or other superabsorbents. The polyurethane foam layer is formed of a hydrophilic polyurethane foam available from Systagenix Wound Management Ltd. under the Registered Trade mark TIELLE. It is produced as described in EP-A-0541391.

The dressing 1 further comprises an apertured wound-facing top sheet 10 that covers the absorbent island and extends around the edges of the absorbent island so that it adheres to the margins of the adhesive-coated backing sheet around the absorbent island. The top sheet 10 is smaller than the backing sheet 2, whereby a relatively narrow adhesive-coated margin 12 of the backing sheet extends around all edges of the top sheet 10.

The top sheet 10 is formed from an apertured film substrate 14 coated on its wound facing surface with a laser of silicone elastomer 16. The film substrate is formed of polyurethane, has thickness about 10 µm. The circular apertures of diameter 6 mm are arranged in a regular array at 10,000 apertures per $m^2$ such that the open area of the film substrate is about 28%. The thickness/coating weight of the silicone is about 50 $g/m^2$. The resulting overall thickness of the top sheet is about 80 µm. The relatively large aperture size and low thickness of the top sheet 10 enable pressure-sensitive adhesive from the laser 4 to penetrate through the apertures and adhere to skin located below the top sheet 10. The degree of adherency can be controlled by varying the tackiness of the silicone elastomer, the size of the apertures, and the overall open area of the top sheet, thereby allowing optimization of adherency for leak prevention and secure attachment versus ease of removal and repositionability. In this embodiment, the additional narrow adhesive margin 16 around the top sheet is provided for further leak prevention from the dressing. In other embodiments, the top sheet may be conterminous with the backing sheet so that there is no narrow adhesive margin 16.

Figure 3:
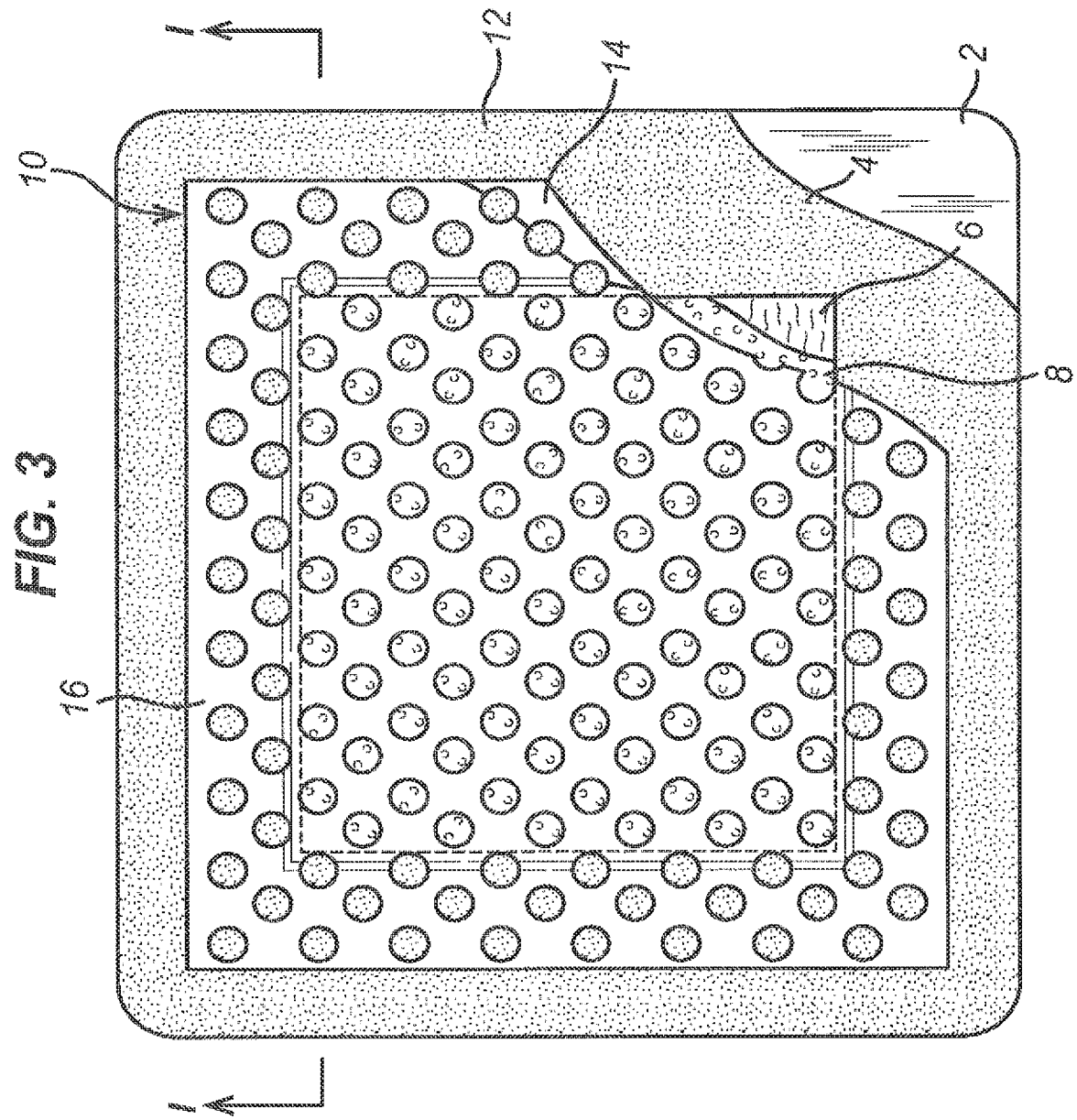
FIG. 3 shows a bottom perspective view of a dressing according to FIG. 1, partially cut away to show detail.

Referring to FIG. 3, release-coated cover sheets 20,22 are positioned over the wound facing side of the dressing. Inside edges 24,26 of the cover sheets 20,22 are folded over to provide for easy removal of the cover sheets before application of the dressing.

Figure 4:
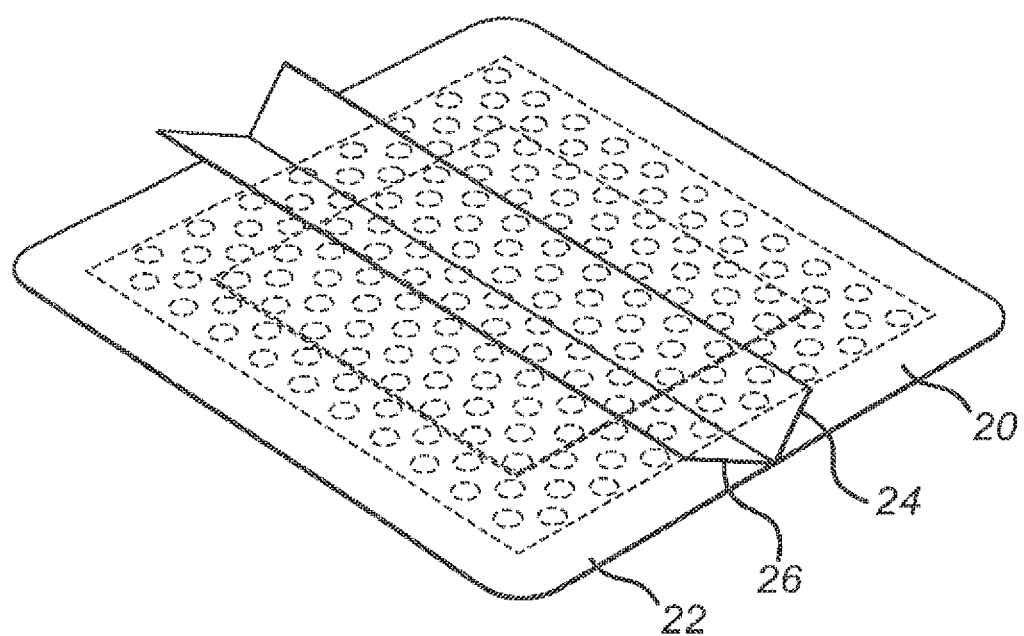
FIG. 4 shows a bottom perspective view of a dressing according to FIG. 1 further comprising a cover sheet.

Referring to FIG. 4, the wound dressing of FIG. 3 is shown sterile and packaged in a microorganism-impermeable envelope 30 having a transparent window 32.

Figure 5:
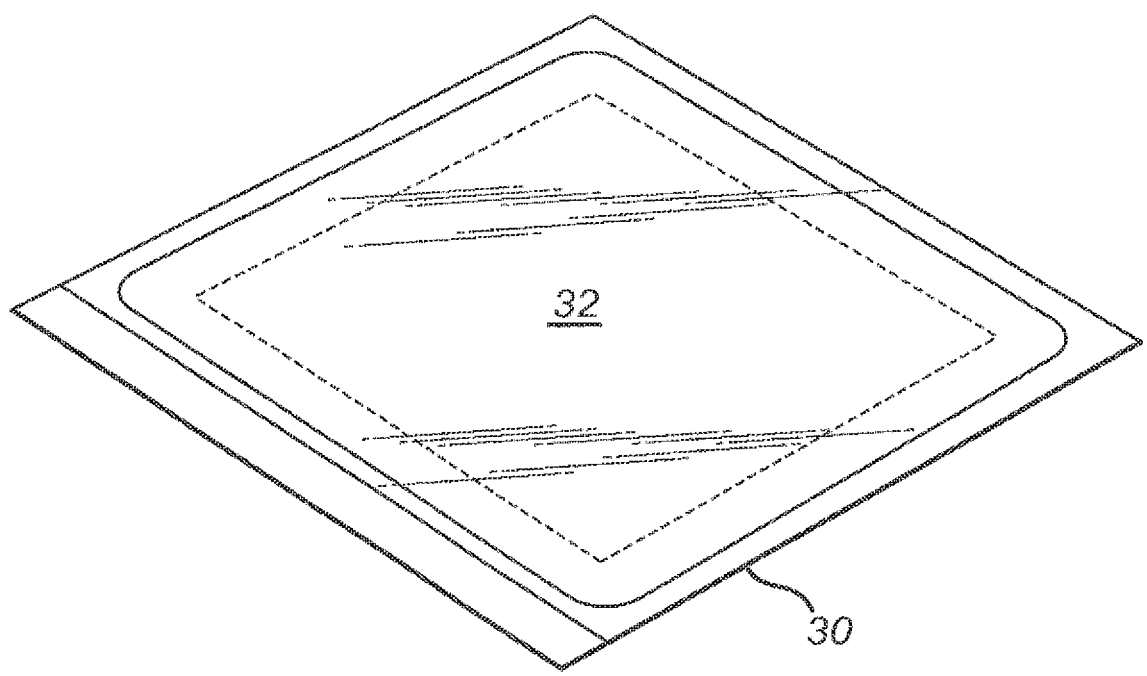
FIG. 5 shows the dressing of FIG. 3 enclosed in a microorganism-impermeable pouch.

Referring to FIG. 5, this embodiment 40 of the apertured wound facing sheet consists of an apertured polymer film substrate layer 42 and silicone coating layer 44 as described above in relation to the first embodiment. Lines of perforations 45,46,47,48 are formed in the film substrate laser 42 parallel to the four edges of the wound facing sheet, to define respective tear stops along each edge. Respective pull tabs 51,52,53,54 are formed integrally with the film substrate layer for removal of the tear strips. A release coating of non-adherent silicone or fluoropolymer may be provided on the surface of the tear strips, opposite the silicone-coated wound facing surface to assist removal of the tear strips in use, as described below.

Referring to FIG. 6, the wound dressing 60 according to this embodiment comprises a PSA coated backing sheet 62, and absorbent island 64, and release-coated cover sheets 65,66 as described above in relation to the first embodiment. The apertured wound facing sheet 40 as shown in FIG. 5 completely covers the backing sheet 62. The dressing may be used in this configuration by removing the cover sheets 65,66 and applying the dressing around a wound. The PSA-coated margin of the backing sheet 62 is completely covered by the apertured wound facing sheet, whereby the overall adherence of the margin is reduced to allow easy removal and/or repositioning of the dressing. For wounds requiring stronger adherency, the tear strips on the apertured wound facing layer may be removed by pulling on the tabs 50,51,52,53 to expose a margin of the PSA coated backing sheet extending around the apertured wound facing sheet.

Figure 8:
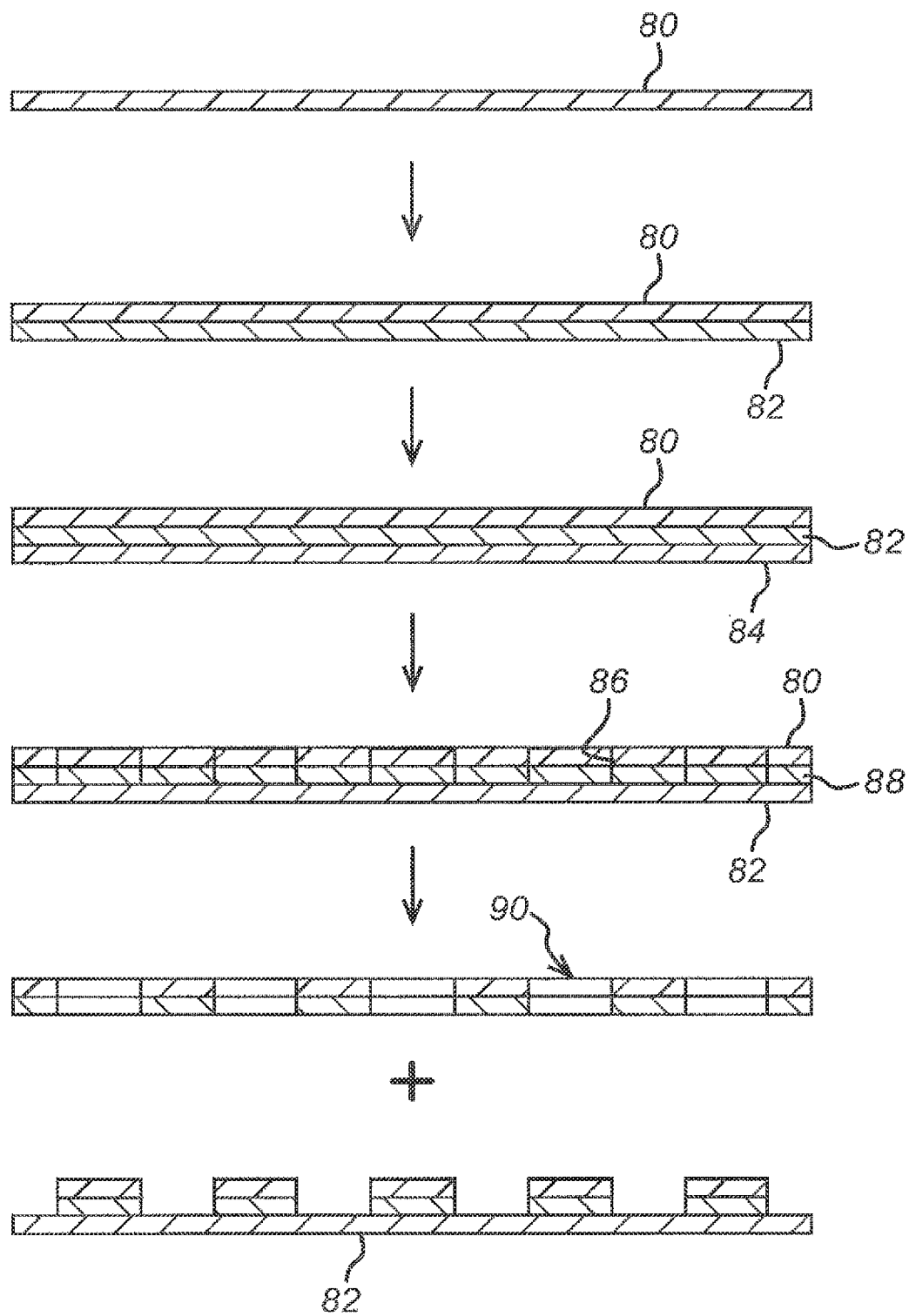
FIG. 8 shows a schematic view of a method according to the invention of making the silicone-coated apertured top sheet.

Referring to FIG. 8, the steps in the preparation of the apertured wound facing sheet according to this embodiment start from a release sheet 80 of a polymeric film material. This is coated with a layer 82 of the fluid silicone precursor composition as described below. The coating may be done by any conventional means such as spraying, roller and/or doctor blade. A layer 84 of the substrate film material is then laminated over the fluid silicone layer. The laminate is then heated to thermally cure the silicone elastomer by passing through an oven held at 150° C. Typical conditions are 5 passes at 4.2 m/min, total residence time 1.5 minutes. This results in thermal partial cure of the silicone coating. The material is then allowed to cool. The resulting cured laminate passes through a die cutter that makes circular cuts 86 through the substrate film material 84 and the cured silicone layer 88, but not through the release sheet 80. The release sheet 80 is then peeled from the silicone layer to separate the apertured coated substrate 90 from the release sheet 80. The silicone and support film from the apertures adheres to the release sheet and is removed with the release sheet 80. The silicone coating composition is prepared by mixing Components A and B of a soft silicone skin adhesive silicone elastomer kit supplied by Dow Corning under product reference Q7-9177. The components are mixed in weight ratio 50:50. Component A comprises a bis-dimethylvinyl terminated polydimethylsiloxane and a platinum catalyst. Component B composes a bis-hydride terminated polydimethylsiloxane. To the mixture is added 2-methyl-3-butyn-2-ol inhibitor at a concentration of 0.02 wt %.

Alternatively, and again with reference to FIG. 8, the release sheet 80 of a polymeric film material is coated with a layer 82 of the fluid silicone precursor composition by any conventional means such as spraying, roller and/or doctor blade and the coated film is then heated to thermally cure the silicone elastomer by passing through an oven held at 150° C. Typical conditions are 1 pass at 0.8 m/min, total residence time 1.5 minutes. This results in thermal cure of the silicone coating. Layer 84 of the substrate film material is then laminated over the silicone layer. The material is then allowed to cool. The resulting cured laminate passes through a die cutter that makes circular cuts 86 through the substrate film material 84 and the cured silicone layer 88, but not through the release sheet 80. The release sheet 80 is then peeled from the silicone layer to separate the apertured coated substrate 90 from the release sheet 80. The silicone and support film from the apertures adheres to the release sheet and is removed with the release sheet 80. The silicone coating composition is prepared by mixing Components A and B of a soft silicone skin adhesive silicone elastomer kit supplied by Dow Corning under product reference Q7-9177. The components are mixed in weight ratio 50:50. Component A comprises a bis-dimethylvinyl terminated polydimethylsiloxane and a platinum catalyst. Component B comprises a bis-hydride terminated polydimethylsiloxane.

The above embodiments have been described by way of example only. It is understood that many other embodiments falling within the scope of the accompanying claims will be apparent to the skilled reader. All publications, patents, and patent applications cited herein are hereby incorporated by reference in their entirety for all purposes.

The invention claimed is:
1. A wound dressing comprising:
a backing sheet;
an island of absorbent material on a central region of the backing sheet;
a pressure-sensitive adhesive disposed between the backing sheet and the island and coupling the island to the backing sheet, and on at least a portion of the backing sheet around the island; and
an apertured layer having at least two apertures and a wound-facing side coated with a silicone elastomer;

wherein the apertured layer is adhered to the backing sheet by the pressure-sensitive adhesive and is configured to allow a portion of the pressure-sensitive adhesive through the apertures to contact skin of a user when the wound dressing is applied to the user; and wherein the apertured layer comprises lines of weakness substantially parallel to, and spaced from, one or more edges of the apertured layer defining a tear-off strip or strips along one or more edges of the apertured layer.

2. The wound dressing according to claim 1, wherein the apertured layer comprises apertures positioned substantially in a uniform array.

3. The wound dressing according to claim 1, wherein a thickness of the apertured layer is less than 1 mm.

4. The wound dressing according to claim 1, wherein the apertured layer further comprises an apertured substrate.

5. The wound dressing according to claim 4, wherein the silicone elastomer is coated on a first side of the apertured substrate.

6. The wound dressing according to claim 4, wherein the apertured substrate is an apertured film.

7. The wound dressing according to claim 1, further comprising:
 a margin of the pressure-sensitive adhesive around the island of absorbent material;
 wherein the island of absorbent material is positioned between the backing sheet and the apertured layer.

8. The wound dressing according to claim 7, wherein the island of absorbent material comprises an absorbent layer and a polyurethane foam layer.

9. The wound dressing according to claim 8, wherein the absorbent layer comprises a nonwoven textile formed of viscose fibers mixed with gel-forming fibers.

10. The wound dressing according to claim 8, wherein the polyurethane foam layer comprises a hydrophilic polyurethane foam.

11. The wound dressing according to claim 7, wherein the margin of the pressure-sensitive adhesive extends around the apertured layer to form an adhesive-coated border.

12. The wound dressing according to claim 11, wherein a portion of the margin of the pressure-sensitive adhesive covered by the apertured layer has a mean width of from 5 mm to 30 mm, and the adhesive-coated border has a mean width of from 2 mm to 20 mm.

13. The wound dressing according to claim 1, wherein a pull tab is attached to, or formed integrally with, each of the tear-off strip or strips to assist removal of the tear-off strip or strips.

14. The wound dressing according to claim 1, wherein the silicone elastomer is a hydrophobic silicone polymer.

15. The wound dressing according to claim 1, wherein the apertured layer comprises an open area of from 5% to 75% of a total area of the apertured layer.

16. The wound dressing according to claim 1, wherein the apertured layer comprises apertures having an open area of from 2 $mm^2$ to 100 $mm^2$.

17. The wound dressing according to claim 15, wherein the apertured layer comprises apertures of which at least about 90% have an open area of from 5 $mm^2$ to 50 $mm^2$.

18. A wound dressing comprising an apertured layer comprising an apertured polymeric film support layer and a coating of silicone elastomer disposed on a first surface of the apertured polymeric film support layer, and wherein the apertured layer comprises a line or lines of weakness substantially parallel to, and spaced from, one or more edges of the apertured layer defining a tear-off strip or strips along one or more edges of the apertured layer, wherein the tear-off strip or strips comprise a release coating on a second surface of the aperture layer opposite the first surface of the aperture layer, wherein the apertured layer comprises apertures having an open area of from 2 $mm^2$ to 100 $mm^2$.

19. The wound dressing of claim 18, wherein the apertured layer further comprises apertures positioned substantially in a uniform array.

20. The wound dressing of claim 18, wherein a thickness of the apertured layer is less than about 1 mm.

21. The wound dressing of claim 18, wherein a thickness of the apertured layer is between 0.02 mm and 0.5 mm.

22. The wound dressing of claim 18, further comprising:
 a backing sheet;
 a layer of pressure-sensitive adhesive disposed on at least a portion of the backing sheet; and
 an island of absorbent material having a smaller area than the backing sheet;
 wherein the backing sheet comprises a margin of the pressure-sensitive adhesive around the island of absorbent material;
 wherein the island of absorbent material is positioned between the backing sheet and the apertured layer.

23. The wound dressing of claim 22, wherein the island of absorbent material comprises an absorbent layer and a polyurethane foam layer.

24. The wound dressing of claim 23, wherein the absorbent layer comprises a nonwoven textile formed of viscose fibers mixed with gel-forming fibers.

25. The wound dressing of claim 23, wherein the polyurethane foam layer comprises a hydrophilic polyurethane foam.

26. The wound dressing according to claim 18, wherein a pull tab is attached to, or formed integrally with, each of the tear-off strip or strips to assist removal of the tear-off strip or strips.

27. The wound dressing according to claim 18, wherein an open area of the apertured layer is from 5% to 75% of a total area of the apertured layer.

* * * * *